United States Patent
Lindh, Sr.

(10) Patent No.: US 8,715,320 B2
(45) Date of Patent: *May 6, 2014

(54) BRAIDED BARBED SUTURE

(71) Applicant: Ethicon, Inc., Somerville, NJ (US)

(72) Inventor: David C. Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,612

(22) Filed: Sep. 17, 2012

(65) Prior Publication Data

US 2013/0066369 A1    Mar. 14, 2013

Related U.S. Application Data

(63) Continuation of application No. 11/169,869, filed on Jun. 29, 2005, now Pat. No. 8,663,277.

(51) Int. Cl.
    *A61B 17/04*    (2006.01)
(52) U.S. Cl.
    USPC .......................................................... 606/228
(58) Field of Classification Search
    USPC .................... 606/228, 230; 602/41–43, 51
    See application file for complete search history.

(56) References Cited

U.S. PATENT DOCUMENTS

| | | | |
|---|---|---|---|
| 2,094,578 A | 10/1937 | Blumenthal et al. |
| 3,123,077 A | 3/1964 | Alcamo |
| 3,130,728 A | 4/1964 | Pearson et al. |
| 3,187,752 A | 6/1965 | Glick |
| 3,208,125 A | 9/1965 | Hall et al. |
| 3,494,006 A | 2/1970 | Brumlik |
| 3,700,544 A | 10/1972 | Matsui |
| 3,709,263 A | 1/1973 | Jackson et al. |
| 3,716,058 A | 2/1973 | Tanner, Jr. |
| 3,720,055 A | 3/1973 | de Mestral et al. |

(Continued)

FOREIGN PATENT DOCUMENTS

| | | |
|---|---|---|
| DE | 1810800 | 6/1970 |
| EP | 1075843 B1 | 2/2005 |

(Continued)

OTHER PUBLICATIONS

Dattilo, P.P. Jr. et al. "Tissue Holding Performance of Knotless Absorbable Sutures", Society for Biomaterials 29th Annual Meeting Transactions (2003) p. 101.

(Continued)

*Primary Examiner* — Gregory Anderson
*Assistant Examiner* — Christina Lauer

(57) ABSTRACT

A suture assembly and a method for making the same is provided. The suture assembly includes a plurality of unbarbed filamentary elements intertwined with one another and at least one barbed filamentary element having a longitudinal axis and having plurality of barbs extending outwardly therefrom in a first direction less than 90 degrees from the longitudinal axis. According to exemplary embodiments, the at least one barbed filamentary may be intertwined along its length with the plurality of unbarbed filamentary elements, and the plurality of barbs extending outwardly beyond the unbarbed filamentary elements, or the primary outer periphery of the at least one barbed filamentary element may be contained within the intertwined unbarbed filamentary elements with the plurality of barbs extending through and outwardly from the plurality of unbarbed filamentary elements.

11 Claims, 10 Drawing Sheets

(56) References Cited

U.S. PATENT DOCUMENTS

| | | |
|---|---|---|
| 3,833,972 A | 9/1974 | Brumlik |
| 3,845,641 A | 11/1974 | Waller |
| 3,847,156 A | 11/1974 | Trumble |
| 3,981,051 A | 9/1976 | Brumlik |
| 4,043,344 A | 8/1977 | Landi et al. |
| 4,546,769 A | 10/1985 | Planck et al. |
| 4,548,202 A | 10/1985 | Duncan |
| 4,640,178 A | 2/1987 | Kurzbock |
| 4,662,886 A | 5/1987 | Moorse et al. |
| 4,900,605 A | 2/1990 | Thorgersen et al. |
| 4,946,467 A | 8/1990 | Ohi et al. |
| 5,128,197 A | 7/1992 | Kobayashi et al. |
| 5,269,783 A | 12/1993 | Sander |
| 5,342,376 A | 8/1994 | Ruff |
| 5,395,126 A | 3/1995 | Tresslar |
| 5,593,424 A | 1/1997 | Northrup, III |
| 5,683,417 A | 11/1997 | Cooper |
| 5,931,855 A | 8/1999 | Buncke |
| 5,964,783 A | 10/1999 | Grafton et al. |
| 6,241,747 B1 | 6/2001 | Ruff |
| 6,475,229 B1 | 11/2002 | Pagedas |
| 6,506,197 B1 | 1/2003 | Rollero et al. |
| 6,599,310 B2 | 7/2003 | Leung et al. |
| 6,645,226 B1 | 11/2003 | Jacobs et al. |
| 8,267,961 B2 | 9/2012 | Popadiuk et al. |
| 2003/0001407 A1 | 1/2003 | Hoshikawa et al. |
| 2003/0041426 A1 | 3/2003 | Genova et al. |
| 2003/0069602 A1 | 4/2003 | Jacobs et al. |
| 2003/0074023 A1 | 4/2003 | Kaplan et al. |
| 2003/0149447 A1 | 8/2003 | Morency et al. |
| 2004/0060410 A1 | 4/2004 | Leung et al. |
| 2004/0088003 A1 | 5/2004 | Leung et al. |
| 2004/0138683 A1 | 7/2004 | Shelton et al. |
| 2004/0193121 A1 | 9/2004 | Kadziauskas et al. |
| 2004/0193191 A1 | 9/2004 | Starksen et al. |
| 2004/0237736 A1* | 12/2004 | Genova et al. ............... 83/13 |
| 2006/0079935 A1 | 4/2006 | Kolster |
| 2007/0005110 A1 | 1/2007 | Collier et al. |
| 2007/0038249 A1 | 2/2007 | Kolster |
| 2007/0219587 A1 | 9/2007 | Accardo |
| 2008/0065203 A1 | 3/2008 | Khalapyan |
| 2008/0132943 A1 | 6/2008 | Maiorino et al. |
| 2009/0105753 A1 | 4/2009 | Greenhalgh et al. |

FOREIGN PATENT DOCUMENTS

| | | |
|---|---|---|
| GB | 1091282 | 11/1967 |
| JP | 63-40559 A | 2/1988 |
| WO | WO 96/06565 A1 | 3/1996 |
| WO | WO 03/017850 A | 3/2003 |
| WO | WO 2004/030704 A2 | 4/2004 |
| WO | WO 2004/030705 A2 | 4/2004 |
| WO | WO 2006/061868 A | 6/2006 |

OTHER PUBLICATIONS

Mc Kenzie, A.R. "An Experimental Multiple Barbed Suture for the Long Flexor Tendsns of the Palm and Fingers", The Journal of Bone and Joint Surgery, (1967) vol. 49B, No. 3, pp. 440-447.

Schmid, A. et al., The outspreading anchor cord. A material for arthroscopic suturing of a fresh anterior cruciate ligament rupture.

International Search Report dated Nov. 24, 2006 for PCT/US2006/024186.

International Search Report dated Jan. 10, 2007 for PCT/US2006/024135.

* cited by examiner

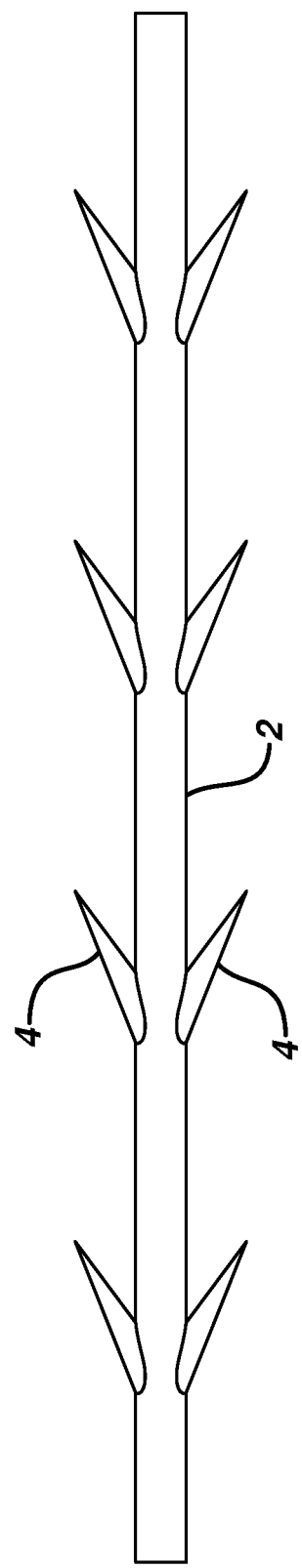

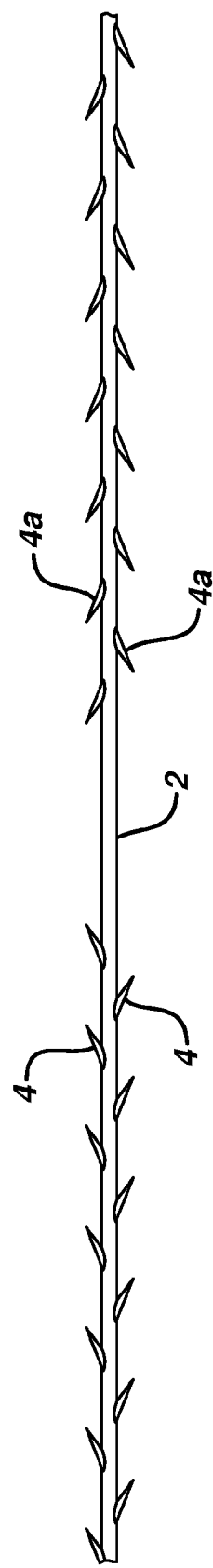

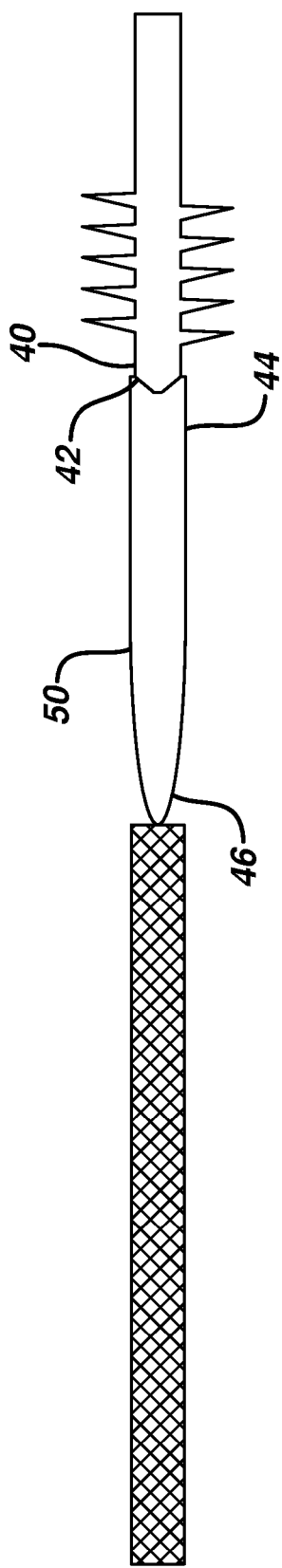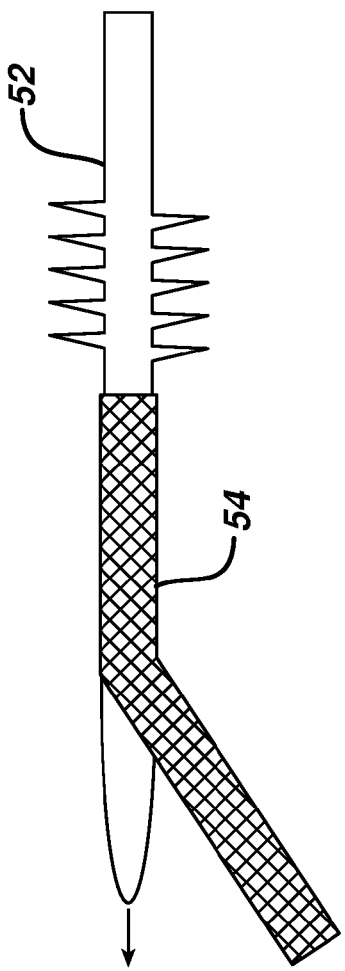

BRAIDED BARBED SUTURE

CROSS REFERENCE TO RELATED APPLICATIONS

The present application is a continuation of U.S. patent application Ser. No. 11/169,869, filed on Jun. 29, 2005.

FIELD OF THE INVENTION

The present invention relates generally to the field of surgical sutures, and more particularly to a surgical suture assembly having a braided, barbed configuration.

BACKGROUND

It is well known that many wounds and surgical incisions are closed using surgical sutures of some sort. Sutures are also commonly used in many other surgical applications, such as to repair damaged or severed muscles, vessels, tissue etc. Typically, the suture is attached at one end to a needle, and the needle is drawn through the tissue to form one or more loops holding the tissue together, and subsequently tied off so that the tissue will remain drawn together. Known surgical sutures include both monofilament sutures and braided sutures. It is also known to create barbs in a monofilament suture in an effort to prevent slippage of the suture within the tissue, an example of which is described in U.S. Pat. No. 5,931,855. These monofilament barbed sutures have been used a variety of cosmetic procedures including brow and face-lifts.

Monofilament, barbed sutures, however, become increasingly prone to failure as the required holding strength needed for a particular procedure increases. Since barbed sutures are typically formed by making cuts or slits in the suture using a blade of some sort, the slits act as stress concentration points. In applications where a significant load is placed on the suture, i.e., heart valve repair or replacement procedures and orthopedic applications, a given barb may fail, or begin peeling away from the suture shaft. Once this occurs, due to the fibrous nature of the suture material the barb may be stripped off the suture shaft along a significant length of the suture causing catastrophic failure.

Monofilament sutures all require one or more knots to be tied to secure the suture in place. Knot tying is a labor-intensive, and may significantly contribute to the overall time of a surgical procedure. In addition, in some surgical procedures the existence of the knot itself may be disadvantageous. For example, in mitral valve replacement procedures, a sewing ring surrounds the new valve and is used to sew the valve in place within the valve annulus. A typical procedure may use up to 20 sutures and result in up to approximately 160 knot throws. In addition to being time consuming, this number of knots can adversely affect the profile of the ring, which can interfere with the valve function.

Thus, it would be desirable to provide a suture having an increased holding strength and/or reduces or eliminates the need for knot tying.

SUMMARY OF THE INVENTION

The present invention provides a suture assembly having a plurality of unbarbed filamentary elements intertwined with one another and at least one barbed filamentary element having a longitudinal axis and having plurality of barbs extending outwardly therefrom in a first direction less than 90 degrees from the longitudinal axis. The at least one barbed filamentary element is intertwined along its length with the plurality of unbarbed filamentary elements, and the plurality of barbs extend outwardly beyond the unbarbed filamentary elements.

Also provided is a suture assembly having a plurality of unbarbed filamentary elements intertwined with one another and having longitudinal axis, and at least one barbed filamentary element having a longitudinal axis, a primary outer periphery, and a plurality of barbs extending outwardly beyond the primary outer periphery in a first direction less than 90 degrees from the longitudinal axis thereof. The primary outer periphery of the at least one barbed filamentary element is contained within the intertwined unbarbed filamentary elements, with the plurality of barbs extending through and outwardly from the plurality of unbarbed filamentary elements.

Yet another suture assembly is provided having a plurality of unbarbed filamentary elements intertwined with one another, and at least one barbed filamentary element having a longitudinal axis and a primary outer periphery, and having a first plurality of barbs extending outwardly therefrom beyond the primary outer periphery and in a first direction less than 90 degrees from the longitudinal axis. The unbarbed filamentary elements substantially surround the primary outer periphery of the at least one filamentary element, and wherein the plurality of barbs extend outwardly beyond said unbarbed filamentary elements.

A method for making a suture assembly is also provided including forming a plurality of barbs in a filamentary element, intertwining a plurality of unbarbed filamentary elements to form an unbarbed assembly having a longitudinal axis, and inserting the barbed filamentary element through the unbarbed assembly to form a suture assembly wherein the plurality of barbs extend outwardly from the unbarbed assembly.

Yet another method for making a suture assembly is provided including forming a plurality of barbs in a filamentary element, and intertwining the barbed filamentary element with a plurality of unbarbed filamentary elements to form a suture assembly, wherein the plurality of barbs extend outwardly from the unbarbed filamentary elements.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 2b is a side view of an alternate embodiment having aligned barbs;

FIG. 2c is a side view of another embodiment having two opposed sets of barbs;

FIGS. 4-8 illustrate various steps of one method that may be used to create a suture assembly of the present disclosure;

DETAILED DESCRIPTION

Figure 1:
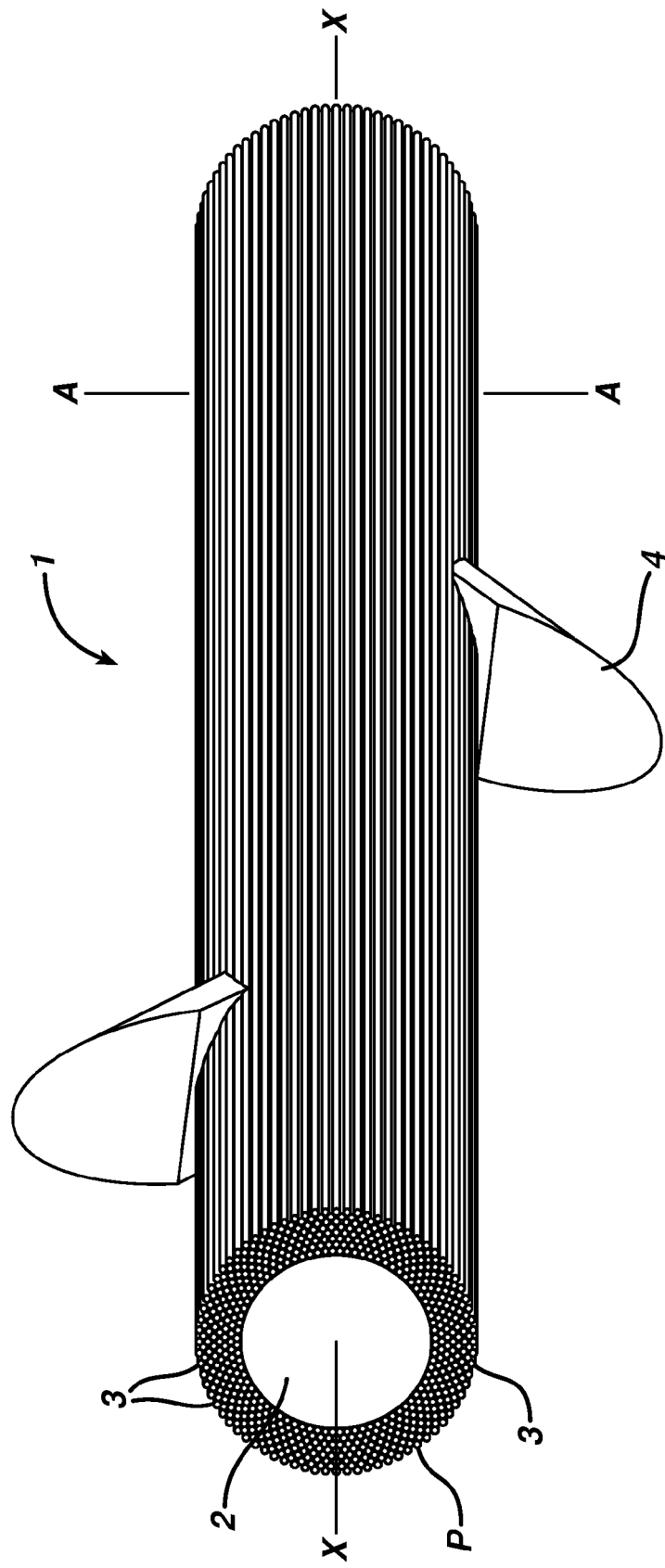
FIG. 1 is a perspective view of one embodiment of a suture assembly according to the present disclosure.

Referring now to FIG. 1, a preferred embodiment of a suture assembly 1 includes at least one barbed filamentary element 2 and a plurality of braided or intertwined unbarbed filaments 3 which will be described further below. The term "braided" is used herein to mean intertwined in any fashion. The barbed filamentary element may be made of any suitable nonabsorbable material such as polypropylene, or any suitable absorbable material such as poly(glycolide-lactide) or poly(glycolide-ε-caprolactone). Alternatively, the barbed filamentary element could be formed from a shape memory polymer, such as polyurethane-based polymers, so as to facilitate deployment of the barbs after exposure to the transition temperature of the shaped memory polymer. In the illustrated embodiment, the barbed filamentary element has a substantially larger cross-section than the unbarbed filaments, and in a preferred embodiment, the barbed filamentary element is formed from a size 0 suture and the unbarbed filamentary elements, in combination, are size 2/0 sutures. Although the barbed filamentary element is illustrated with a substantially circular cross-section, other cross sections may be used as well, such as triangular, rectangular or the like. The term "primary outer periphery" p is used herein to refer to the periphery of the cross-section of the suture assembly as if no barbs were present, such as along line A-A of FIG. 1. As shown in greater detail in FIG. 2a, the barbed filamentary element 2 lies substantially along longitudinal axis x-x, and has a plurality of barbs 4 extending outwardly therefrom in a first direction that is at an angle α relative to the longitudinal axis that is less than 90 degrees.

Figure 2A:
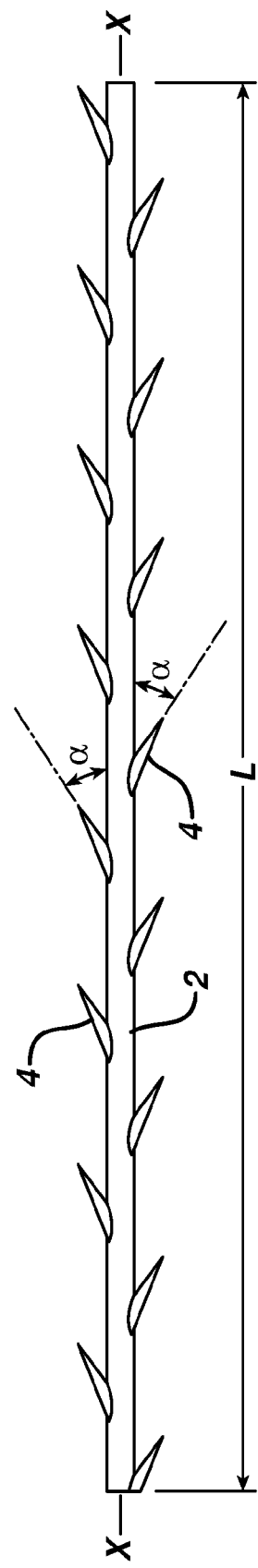
FIG. 2a is a side view illustrating one embodiment having staggered barbs.

The barbs 4 may exist along substantially the entire length L of the filamentary element 2 as shown in FIG. 2a, or along only a portion(s) of the length. Further, any suitable configuration of the barbs relative to filamentary element 2 can be used in the suture assembly of the present invention. For example, the barbs 4 may be staggered around the circumference of the filamentary element in any way (FIG. 2a) or may be aligned along the filamentary element as shown in FIG. 2b. A portion of the length of the filamentary element may also include a second set of barbs 4a facing in a second direction that is greater than 90 degrees from the longitudinal axis of the filament as shown in FIG. 2c. A use for which the configuration of FIG. 2c is advantageous will be described in greater detail below.

Figure 3:
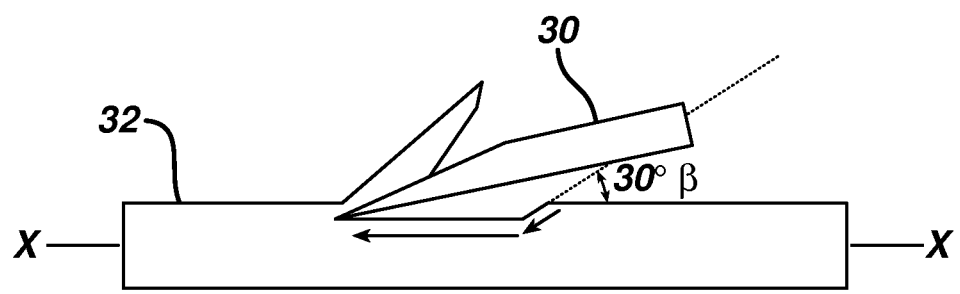
FIG. 3 illustrates cutting dimensions used to create an exemplary barb.

The barbs may be arranged on the monofilament according to any desired configuration, and can be formed using any suitable method including those well known in the art. These methods may include injection molding, stamping, cutting by knife or laser, press forming or the like. According to a preferred method, the barbs are formed by cutting a monofilament suture with any suitable cutting blade or knife. The desired number of acute, angular cuts are made directly into the suture body. FIG. 3 illustrates an exemplary cut, where the cutting blade 30 first cuts into the monofilament 32 at an angle β of approximately 30 degrees relative to the longitudinal axis x-x of the monofilament to a depth of approximately 0.08 inches, and subsequently further cuts into the monofilament for a distance of approximately 0.024 inches at an angle of approximately 0 degrees. To achieve this cutting, the monofilament is typically placed and held on a cutting vice or the like in a manner well known in the art. A template may also be used to help guide the cutting blade.

Following creation of the barbed monofilament and the intertwined unbarbed filaments, the suture assembly 1 is formed by joining the barbed and unbarbed filaments. According to one exemplary method for accomplishing this, one end 40 of the barbed monofilament is inserted into a hollow recess 42 in the distal end 44 of a needle (opposite the pointed end 46) as shown in FIG. 4. The end 40 of the suture may be held in place within the hollow recess of the needle by any suitable means, such as by crimping the end of the needle around the suture or using adhesive or the like. Further, as an alternative, the suture end may be inserted into a cannula, sheath or any other suitable means by which to draw it through a braided suture as described below. The latter means may additionally function to protect the barbs as they are drawn through the braided filament.

Figure 6:
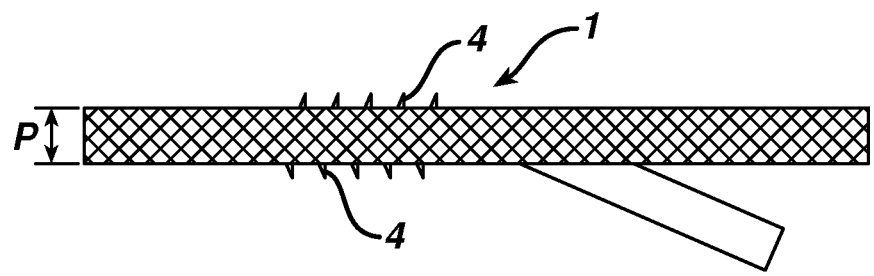
Figure 7:
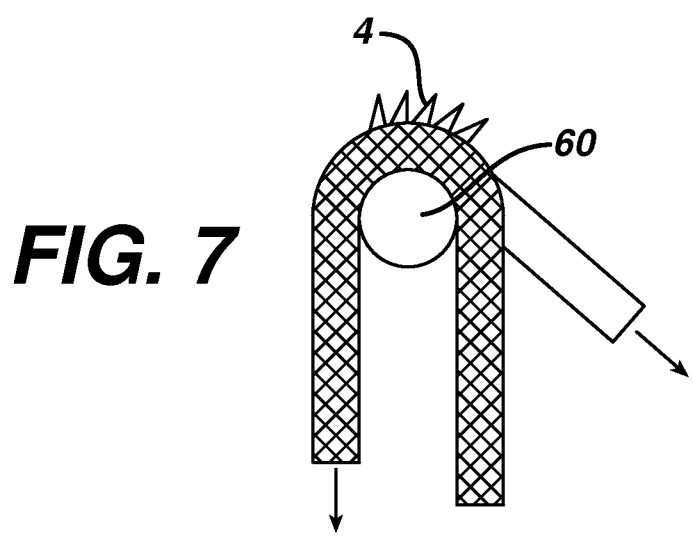
Figure 8:
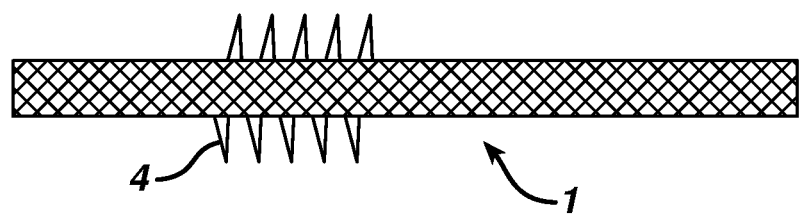

The needle 50 is then used to draw the barbed monofilament 52 through the core of the intertwined unbarbed monofilaments 54 as shown in FIG. 5. The needle (or cannula) is then removed leaving the assembly 1 as shown in FIG. 6. The barbs 4 will tend to extend outwardly from the barbed monofilament, with some extending outwardly beyond the primary outer periphery p of the intertwined unbarbed monofilaments. To further enhance the projection of the barbs, however, it may be desirable to wrap the assembly over a mandrel 60 as shown in FIG. 7. Tension is then applied as indicated by the arrows in FIG. 7, which causes the barbs to project fully as shown in FIG. 8. In order to firmly secure the ends of the barbed monofilament within the intertwined, unbarbed filaments, heat, pressure, and/or adhesive may subsequently be applied to cause bonding between them.

In an alternate embodiment, the unbarbed monofilaments may be joined with the barbed filament by braiding directly with the barbed filament, or braiding directly with a plurality of barbed filaments. To help prevent loosening of the assembly and/or to facilitate passage of the suture assembly through tissue or the like, one or more of the monofilaments can be coated or heat set to hold the assembly together. For example, heat could be applied at each end of the suture assembly using a heated die or the like. Exemplary coatings could include polyester resins or polyvinyl acetate.

The suture assemblies described above are suitable for use in a variety of surgical procedures, including those in which prosthetic devices are secured to tissue. Exemplary procedures are heart valve replacement procedures, one of which will now be described in detail. In current mitral valve replacement procedures, a surgical incision is made in the patient's chest, typically through a full median sternotomy. Cardiopulmonary bypass is then established, by inserting cannulae into the superior and inferior vena cavae for venous drainage and into the ascending aorta for arterial perfusion, with the cannulae being connected to a heart-lung machine. Once cardiopulmonary bypass and cardiac standstill have been achieved, the mitral valve is exposed by entering the left atrium and retracting the atrial tissue away using sutures or retraction devices. The atriotomy (entry incision) is usually made in the right side of the left atrium, anterior to the right pulmonary veins, although other approaches may be used.

Once access is obtained and the condition evaluated, valve replacement is performed using one of several different well known techniques to secure the prosthesis to the annulus, including interrupted mattress sutures, a continuous running suture, interrupted simple (non-mattress) sutures, or specialized clips or staples. The most common technique is the interrupted suture technique, with one such technique being illustrated in FIGS. 9a-9d. A plurality of double-needle suture assemblies 900 according to the present invention are used for the repair. As illustrated best in FIG. 9b, the suture assemblies include a first portion 910 along which a first set of barbs 912 are formed to face in one direction, and a second portion 914 along which a second set of barbs 916 face in a second direction that preferably is towards the first set of barbs.

All stitches 904 are placed through the prosthetic valve 906 before approximation of the prosthesis to the valve annulus 908. Interrupted mattress stitches using a suture assembly of the present invention, preferably of alternating color, are used. Compressed Teflon® felt pledgets 902 may be used to strengthen the repair. The mattress stitches are placed through the sewing ring of the prosthesis and then through the mitral annulus posteriorly, incorporating the chordae tendineae. The Teflon® pledgets are then threaded on separately. The initial stitches are preferably placed superiorly on the annulus, working inferiorly in a counterclockwise fashion as shown.

Figure 9A:
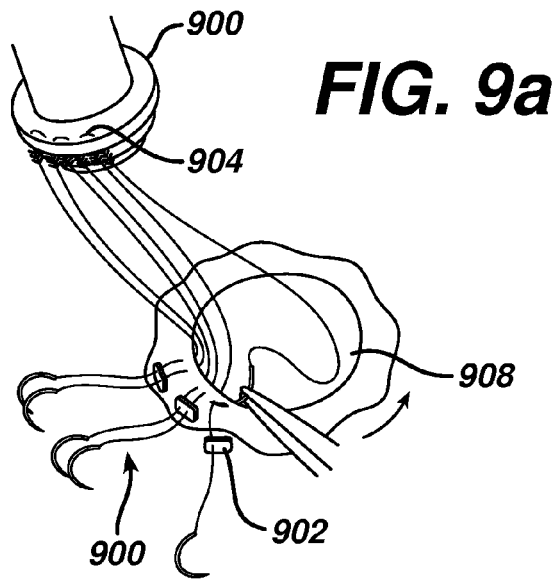
FIGS. 9a-9d illustrate various steps in an exemplary heart valve replacement procedure using a suture assembly of the present disclosure.
Figure 9B:
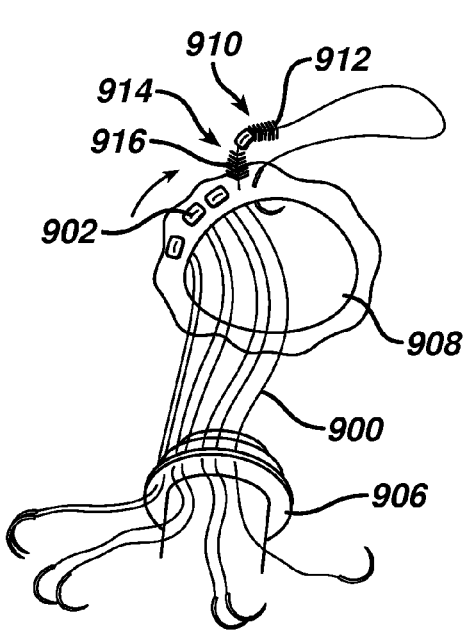
Figure 9C:
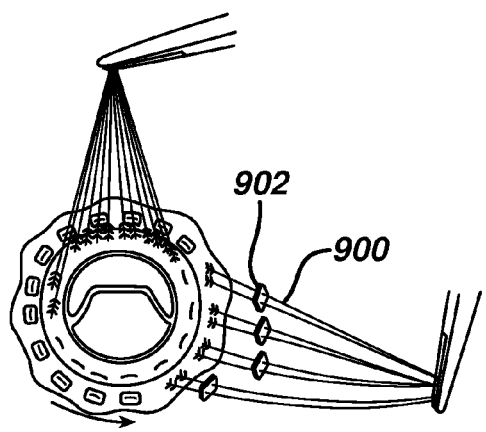
Figure 9D:
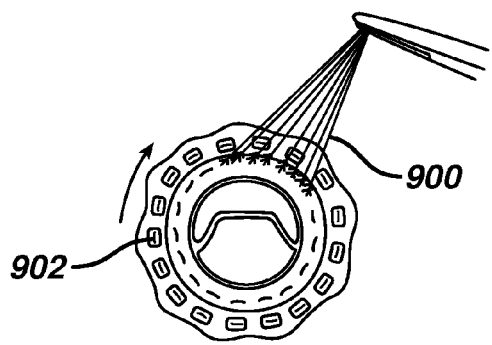

Following completion of the sutures on the posterior half of the mitral annulus, the valve prosthesis is drawn to the right side, and stitches are placed through the anterior portion of the annulus beginning superiorly and working inferiorly in a clockwise fashion as shown in FIG. 9b. The stitches are taken from the atrial surface through the mitral annulus and then brought through the sewing ring of the prosthesis. Traction on the sutures provides exposure for subsequent stitches, and Teflon® pledgets are preplaced centrally on the double needle sutures. Following placement of all sutures, strong traction is placed on the sutures as the valve prosthesis is slid over them into the annulus of the mitral valve as shown in FIG. 9c.

In traditional replacement procedures with prior art sutures, the sutures are then each tied in the same order in which they were placed, beginning posteriorly and working in a counterclockwise fashion. The anterior sutures are then tied in a clockwise fashion to complete the repair. Thus, typical mitral valve replacement procedures involve multiple suture knots, on the order of 12-16 (approximately 60 to 112 knot throws assuming approximately 5-7 throws per knot), with each knot taking approximately 20-30 seconds to perform. In addition, each knot must be secure and tightly fixate the ring to the annular tissue to avoid leakage. By utilizing a barbed suture or barbed suture assembly as described and illustrated, however, the valve replacement procedure is greatly simplified in that the time and difficulty required for knot tying is reduced. As shown, the unbarbed portions of the suture assembly ensure that the prosthetic valve can easily be parachuted into position relative to the valve annulus. Upon final positioning of the ring, however, as the prosthetic valve slides over the barbed regions of the suture assembly it becomes secure. If desired, an additional bite may be taken through the sewing ring to further secure the ring.

Figure 10:
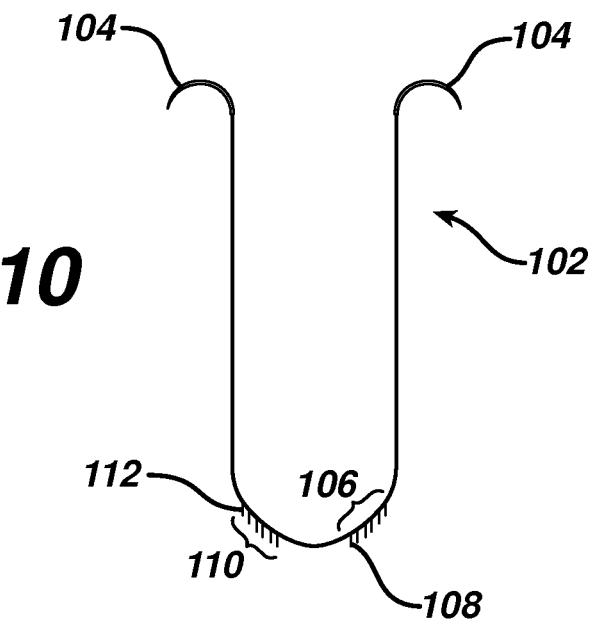
FIGS. 10 and 11 illustrate various embodiments of suture assemblies according to the present disclosure.
Figure 11:
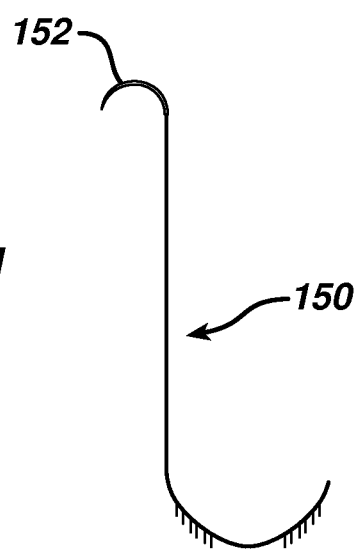

FIG. 10 illustrates in greater detail a suture assembly of the present invention that can be used, for example, in the valve replacement procedure set forth in FIGS. 9a-9d. In FIG. 10, the suture assembly 102 extends between two suture needles 104. A first portion of the length 106 includes a first set of barbs 108 that extend outwardly in a first direction and a second length 110 includes a second set of barbs 112 that extend outwardly in a second direction that is towards the first set of barbs as shown. The braided suture assembly may be formed in various ways as described above. FIG. 11 illustrates a suture assembly 150 that is attached at only one end to a single needle 152 and with no unbarbed length at the second end. In a mitral valve replacement procedure, this design would require that the surgeon pass the needle down through the sewing ring before biting through the tissue surrounding the annulus, and then subsequently pass the needle back through the ring before securing the ring against the tissue.

Figure 12:
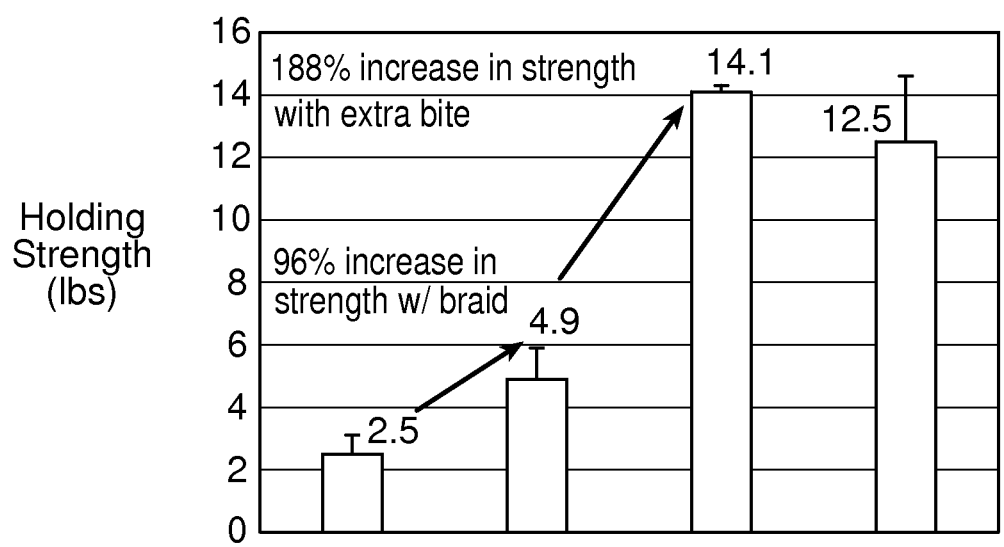
FIG. 12 is a chart illustrating relative holding strengths of a barbed suture according to the present disclosure and various other sutures.

Test results have demonstrated a significantly improved holding strength using the suture assembly of the present invention as compared to a barbed monofilament. The chart set forth in FIG. 12 illustrates these results. The first bar on the left represents the holding strength of a double-armed barbed PROLENE suture (a polypropylene suture manufactured by Ethicon, Inc. of Somerville, N.J.), size 0, when drawn straight through (perpendicular to) a DACRON® sewing ring until the barbs engage the sewing ring. Once engaged, 2.5 lbs. (+/0.6) of force were required to dislodge the suture. The next bar represents the holding strength (4.9 lbs. +/−1.0) of a suture assembly including the same barbed suture as above, within an ETHIBOND, size 2/0, suture, which is a braided Poly(ethylene, terephthalate) suture also manufactured by Ethicon, Inc. The third bar represents the increased holding strength (14.1 +/−0.2) achieved when an extra bite is taken through the sewing ring with the described suture assembly. Finally, the last bar to the right represents the holding strength (12.5 +/−2.1) of an ETHIBOND, size 2/0 suture with an 8 throw knot. As can be seen, the braided, barbed suture assembly has a 96% greater holding strength as compared to the barbed monofilament, and 188% greater holding strength when one additional bite is taken. Further, with just one bite, the holding strength is greater than that of a braided suture with an 8 throw knot. Thus, superior holding strength is achieved without the time and difficulty involved with tying multiple knots.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A barbed monofilament comprising a substantially circular cross-section and a plurality of barbs formed therein by a cut that extends inwardly into the monofilament to a predetermined depth, wherein a distal portion of each barb is defined by a cut extending for a first length at a substantially constant first angle relative to a longitudinal axis of the monofilament, and a proximal portion of each barb is defined by a cut extending for a second length at a second angle of approximately zero degrees relative to the longitudinal axis of the monofilament, wherein the barbed monofilament is comprised of a polymeric material.

2. The barbed monofilament according to claim 1, wherein the first angle is approximately 30 degrees.

3. The barbed monofilament according to claim 1, wherein the predetermined depth is approximately 0.08 inches.

4. The barbed monofilament according to claim 3, wherein the second length is approximately 0.024 inches.

5. The barbed monofilament according to claim 1, wherein the plurality of barbs are formed along a portion of a length of the monofilament.

6. The barbed monofilament according to claim 1, wherein the plurality of barbs are formed along substantially an entire length of said monofilament.

7. The barbed monofilament according to claim 1 wherein the plurality of barbs are staggered around a circumference of the monofilament.

8. The barbed monofilament according to claim 1, wherein said plurality of barbs includes a first set and a second set of barbs, and wherein the barbs of said first set are substantially aligned along a length of said suture, and wherein the barbs of said second set are substantially aligned along a length of said suture.

9. The barbed monofilament according to claim 8, wherein said first and second sets of barbs are aligned substantially opposite one another around a circumference of said monofilament.

10. The barbed monofilament according to claim 1, wherein said monofilament is comprised of a non-absorbable material.

11. The barbed monofilament according to claim 1, wherein the monofilament is comprised of an absorbable material.

* * * * *